United States Patent
Pyzer-Knapp et al.

(10) Patent No.: US 11,923,050 B2
(45) Date of Patent: Mar. 5, 2024

(54) EFFICIENTLY POPULATING A PHASE DIAGRAM FOR MULTIPLE SUBSTANCES

(71) Applicants: United Kingdom Research and Innovation, Swindon (GB); International Business Machines Corporation, Armonk, NY (US)

(72) Inventors: Edward Pyzer-Knapp, Winchester (GB); Richard Anderson, Warrington (GB)

(73) Assignees: United Kingdom Research and Innovation, Swindon (GB); International Business Machines Corporation, Armonk, NY (US)

( * ) Notice: Subject to any disclaimer, the term of this patent is extended or adjusted under 35 U.S.C. 154(b) by 1091 days.

(21) Appl. No.: 16/630,197

(22) PCT Filed: Jul. 11, 2018

(86) PCT No.: PCT/GB2018/051978
§ 371 (c)(1),
(2) Date: Jan. 10, 2020

(87) PCT Pub. No.: WO2019/012279
PCT Pub. Date: Jan. 17, 2019

(65) Prior Publication Data
US 2020/0168301 A1    May 28, 2020

(30) Foreign Application Priority Data
Jul. 12, 2017  (GB) .................................. 1711184

(51) Int. Cl.
G16C 20/30      (2019.01)
G16C 20/70      (2019.01)
G16C 20/80      (2019.01)

(52) U.S. Cl.
CPC ............. *G16C 20/30* (2019.02); *G16C 20/70* (2019.02); *G16C 20/80* (2019.02)

(58) Field of Classification Search
CPC ......... G16C 20/30; G16C 20/70; G16C 20/80
See application file for complete search history.

(56) References Cited

U.S. PATENT DOCUMENTS

| | | | |
|---|---|---|---|
| 9,120,766 B2* | 9/2015 | Bevill | C07D 473/12 |
| 2010/0047527 A1* | 2/2010 | Katter | H01F 1/015 |
| | | | 252/62.55 |

(Continued)

OTHER PUBLICATIONS

Kusne (On-the-fly machine-learning for high-throughput experiments: search for rare-earth-free permanent magnets, 2014) (Year: 2014).*

(Continued)

*Primary Examiner* — Mohammad K Islam
(74) *Attorney, Agent, or Firm* — Lempia Summerfield Katz LLC

(57) ABSTRACT

Method and system are provided for efficiently populating a phase diagram for modeling of multiple substances. The method may include defining an n-way phase diagram with data points each being an n-tuple describing the n substance inputs, wherein the n-way phase diagram is defined at a user-configured resolution. The method may select an initial subset of data points and calculate their contribution to the phase diagram. The method may then generate a Bayesian model based on the initial subset of calculated data points and predicting the resultant phase and an associated uncertainty of all the uncalculated data points in the defined phase diagram. The method may select a sample subset of the data points using maximum entropy sampling and calculating a resultant phase for each of the selected data points, and incorporate the calculated phases into the Bayesian model. Re-modeling the Bayesian model may predict the resultant (Continued)

phase and an associated uncertainty of all the remaining uncalculated data points in the defined phase diagram. Repeating the selecting a sample subset of the data points using maximum entropy sampling and re-modeling is carried out until a defined termination criterion is met.

27 Claims, 8 Drawing Sheets

(56) References Cited

U.S. PATENT DOCUMENTS

| | | | |
|---|---|---|---|
| 2015/0106035 A1 | 4/2015 | Vecchio | |
| 2020/0024693 A1* | 1/2020 | Zhang | B22F 9/04 |
| 2020/0257933 A1* | 8/2020 | Steingrimsson | B22F 12/45 |
| 2022/0336055 A1* | 10/2022 | Hamp | G06N 3/0464 |

OTHER PUBLICATIONS

Beneš O. et al. "Modelling and calculation of the phase diagrams of the LiF-Naf-RbF-LaF3 system", CALPHAD: Computer Coupling of Phase Diagrams and Thermochemistry 31 (2007) 209-216.

Cao W. et al. "PANDAT software with PanEngine, PanOptimizer and PanPrecipitation for multi-component phase diagram calculation and materials property simulation", CALPHAD: Computer Coupling of Phase Diagrams and Thermochemistry 33 (2009) 328-342.

Collins C. et al. "Accelerated discovery of two crystal structure types in a complex inorganic phase field", Nature 546 (2017) 280-298.

International Search Report in International Application No. PCT/GB2018/051978, dated Oct. 5, 2018, 3 pages.

Kattner U. R. "The Thermodynamic Modelling of Multicomponent Phase Equilibria", Journal of the Minerals, Metals & Materials Society 49 (1997) 14-19.

Königsberger E. el at. "Analysis of Phase Diagrams Employing Bayesian Excess Parameter Estimation", Monatshefte Für Chemie / Chemical Monthly 121 (1990) 119-127.

Sebastiani P. et al. "Maximum entropy sampling and optimal Bayesian experimental design", J. R. Statistical Society B 62 (2000) 145-157.

Stan M. et al. "A Bayesian approach to evaluating the uncertainty of thermodynamic data and phase diagrams", Computer Coupling of Phase Diagrams and Thermochemistry 27 (2003) 319-323.

U.K. Search Report in GB1711184.0, dated Dec. 13, 2017, 2 pages.

Zhu R. et al. "Multi-phase microstructure design of a low-alloy TRIP-assisted steel through a combined computational and experimental methodology", Acta Materialia, Elsevier, Oxford 60 (2012) 3022-3033.

* cited by examiner

EFFICIENTLY POPULATING A PHASE DIAGRAM FOR MULTIPLE SUBSTANCES

RELATED APPLICATIONS

The present patent document is a § 371 nationalization of PCT Application Serial No. PCT/GB2018/051978, filed Jul. 11, 2018, designating the United States, which is hereby incorporated by reference, and this patent document also claims the benefit of United Kingdom Application No. GB 1711184.0, filed Jul. 12, 2017, which is also hereby incorporated by reference.

BACKGROUND

The present invention relates to phase diagrams for multiple substances, and more specifically, to efficiently populating a phase diagram for multiple substances. Such a phase diagram may then be used to formulate, for example, a mixture of the multiple substances having desired phase properties.

A phase diagram is a chart used to show conditions (pressure, temperature, volume, concentrations of component substances of a mixture etc.) at which distinct phases, for example thermodynamically distinct phases, of substances occur and coexist at equilibrium. Phase diagrams have use in various fields including physical chemistry, engineering, mineralogy, and materials science. One application is the formulation industry and the sub-domain of liquid formulation.

In the sub-domain of liquid formulation, one of the most important tasks is the construction of a phase diagram, since this will indicate where, for example, mixtures will begin to separate into their constituent components which may be a highly undesirable occurrence. Due to the financial and time expense of performing rigorous phase separation experiments, simulation has begun to be used as a viable alternative for performing initial investigations into the phase diagrams of potential mixtures. Whilst simulations are cheaper and faster than traditional laboratory based experimentation, they still represent a significant computational expense.

SUMMARY

According to an aspect of the present invention there is provided a computer-implemented method for efficiently populating a phase diagram for modeling of multiple substances, the method comprising: defining an n-way phase diagram with data points each being an n-tuple describing the n substance inputs; selecting an initial subset of data points and calculating their contribution to the phase diagram; generating a Bayesian model based on the initial subset of calculated data points and predicting the resultant phase and an associated uncertainty of all the uncalculated data points in the defined phase diagram; selecting a sample subset of the data points using maximum entropy sampling and calculating a resultant phase for each of the selected data points, and incorporating the calculated phases into the Bayesian model; re-modeling the Bayesian model to predict the resultant phase and an associated uncertainty of all the remaining uncalculated data points in the defined phase diagram; and repeating the selecting a sample subset of the data points using maximum entropy sampling and re-modeling until a defined termination criterion is met. The n-way phase diagram may be defined at a user configured resolution.

According to a further aspect of the present invention there is provided a system for efficiently populating a phase diagram for modeling of multiple substances, the system comprising: a processor and a memory configured to provide computer program instructions to the processor to execute the function of the following components; a model template defining component for defining an n-way phase diagram with data points each being an n-tuple describing the n substance inputs; a subset selecting component for selecting an initial subset of data points and calculating their contribution to the phase diagram; a modeling component for generating a Bayesian model based on the initial subset of calculated data points and predicting the resultant phase and an associated uncertainty of all the uncalculated data points in the defined phase diagram and for re-modeling the model during method iterations; and a sampling component for selecting a sample subset of the data points using maximum entropy sampling and calculating a resultant phase for each of the selected data points, and incorporating the calculated phases into the Bayesian model and for repeating the selecting until a defined termination criterion is met. The n-way phase diagram may be defined at a user configured resolution.

According to a further aspect of the present invention there is provided a computer program product for efficiently populating a phase diagram for modeling of multiple substances, the computer program product comprising a computer readable storage medium having program instructions embodied therewith, the program instructions executable by a processor to cause the processor to: define an n-way phase diagram with data points each being an n-tuple describing the n substance inputs, wherein the n-way phase diagram is defined at a user-configured resolution; select an initial subset of data points and calculating their contribution to the phase diagram; generate a Bayesian model based on the initial subset of calculated data points and predicting the resultant phase and an associated uncertainty of all the uncalculated data points in the defined phase diagram; select a sample subset of the data points using maximum entropy sampling and calculating a resultant phase for each of the selected data points, and incorporating the calculated phases into the Bayesian model; re-model the Bayesian model to predict the resultant phase and an associated uncertainty of all the remaining uncalculated data points in the defined phase diagram; and repeat the selecting a sample subset of the data points using maximum entropy sampling and re-modeling until a defined termination criterion is met.

BRIEF DESCRIPTION OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings.

Preferred embodiments of the present invention will now be described, by way of example only, with reference to the following drawings in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

DETAILED DESCRIPTION

Figure 1:
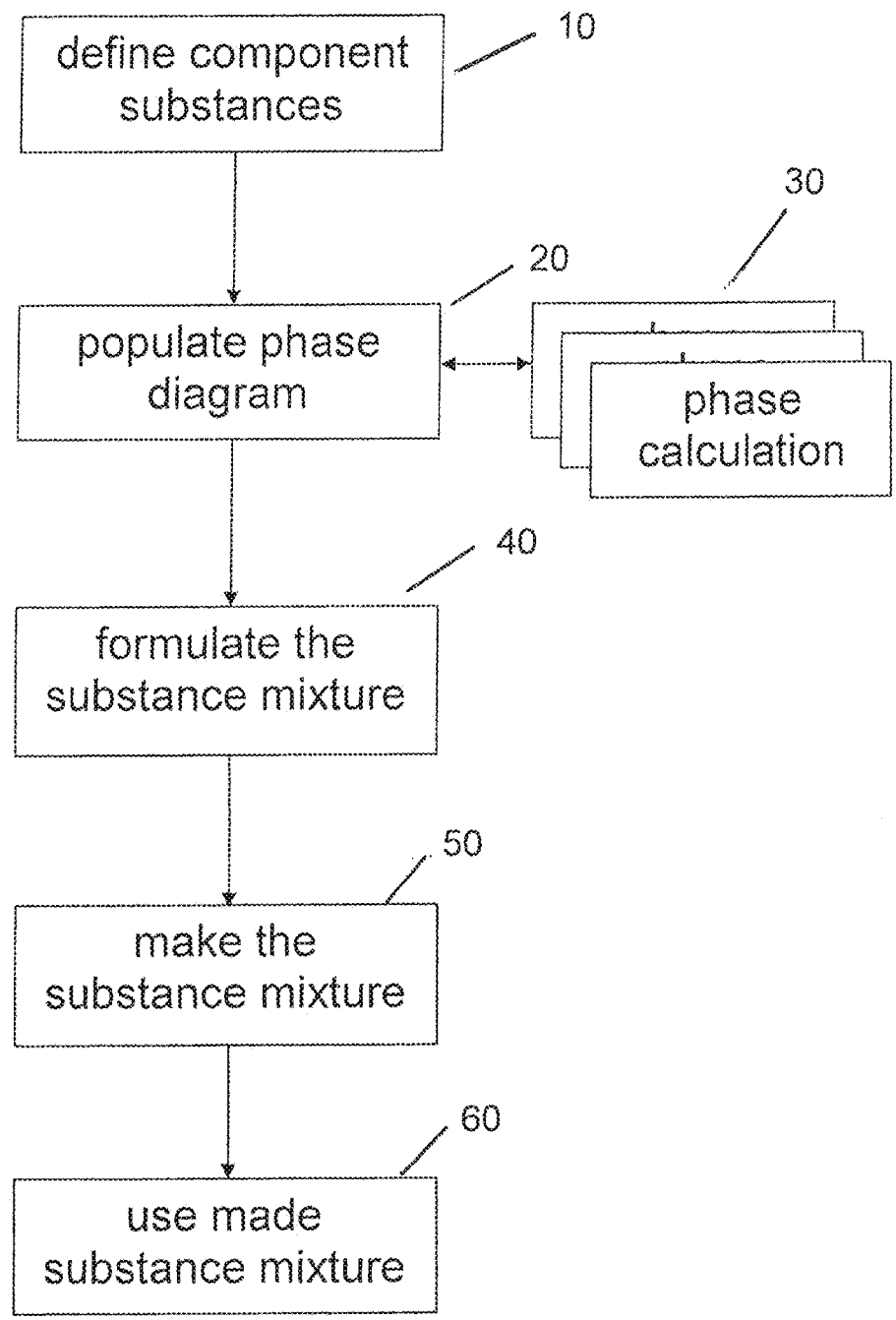
FIG. 1 illustrates how a mixture of substances may be formulated and manufactured using a method or system in accordance with the present invention for example as illustrated in FIG. 2 or 3.

Referring to FIG. 1, embodiments of the invention may be used to formulate or manufacture a mixture of substances such that the mixture has desirable properties in terms of phase. To this end, the method outlined in FIG. 1 provides an initial step 10 of defining which component substances are to be used in the mixture. The component substances may for example be liquids and/or other materials in a mixture to be used as a medicament, as a cosmetic, in home and personal care goods (for example shampoos), as a lubricant or other engineering mixture, a mixture of refrigerant or other fluid components, and so forth. The mixture of materials may be solids in some examples, for example inorganic extended solid structures (crystals).

The mixture may for example comprise both active substances for achieving the intended effect of the mixture, and other substances for improving behaviour, storage properties and so forth such as surfactants, antioxidants and similar.

Having selected the substances for the mixture, a subsequent step 20 is then carried out of populating a phase diagram which represents distinct phases of the mixture, such as a mixture of different liquids, such that the phase of the mixture is defined by the phase diagram as a function of parameters such as concentrations of the substances within the mixture, and/or other parameters such as temperature, pressure, and so forth as desired. For example, the phase diagram may indicate where in the parameter space mixtures of substances begin to separate into their constituent components, an effect which may often be undesirable, or where a mixture adopts a particular desirable or undesirable phase. Some phases which may be determined from the phase calculations for liquid component mixtures could be, as mentioned below, branched worm-like, lamella, hexagonal, isotropic, cubic lattice, rods, worm-like and inverse micellar, and the reverse of these for high surfactant systems.

To this end, where we describe substance inputs these may be considered to be concentrations of each substance or similar measures such as volumes, molar fractions, etc.

The step 20 of populating the phase diagram may be carried out in particular using the methods and apparatus described below, and may typically rely on a fairly large number of steps 30 of particular phase calculations (and/or laboratory experiments) each for a particular parameter combination, for example more than 10, or more than 100 such phase calculations. Some techniques which may be used for such phase calculations are mentioned below, such as molecular dynamics, Monte Carlo simulations, and dissipative particle dynamics. Since both the parameter space and the computational or laboratory effort for each phase calculation 30 may be large, the cost of effectively populating the phase diagram in step 20 is generally high. To this end, embodiments of the invention enable a sufficiently detailed phase diagram, which contains adequate data points where needed, to be generated at lower computational and/or experimental cost.

Figure 4A:
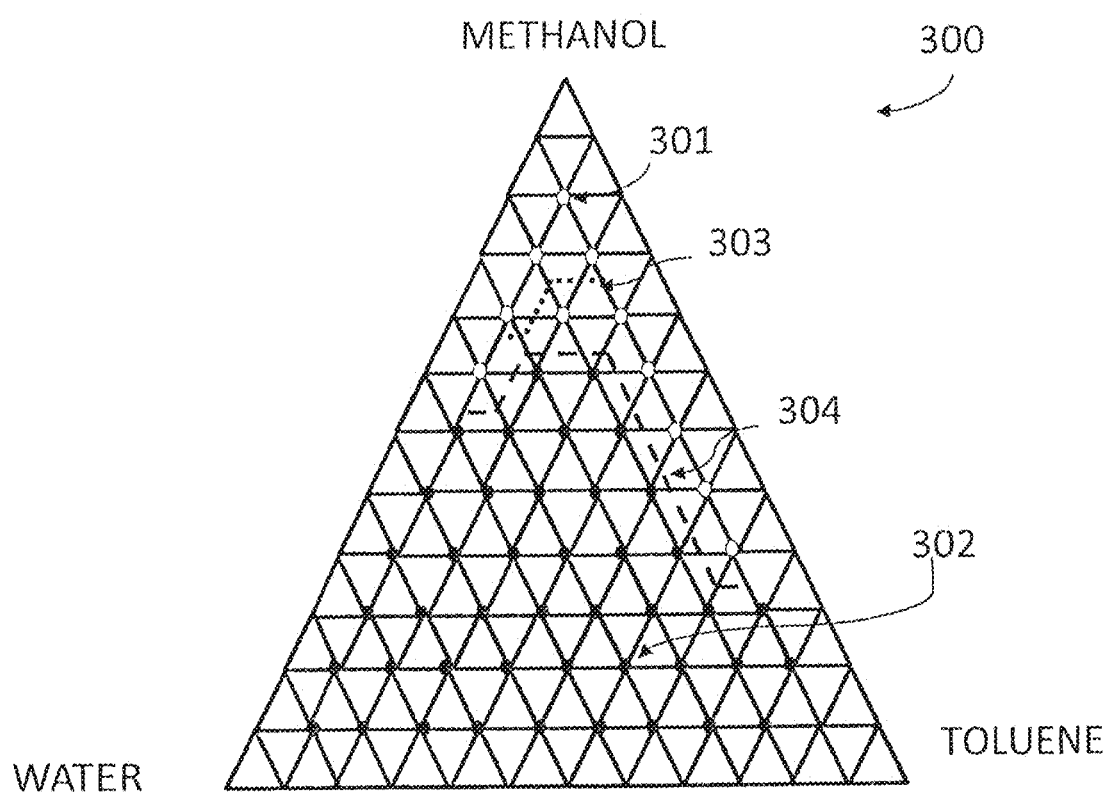
FIGS. 4A and 4B are example phase diagrams showing the population of data points in the prior art and in with the present invention.

For example, in some particular phase diagrams generated by the inventors using computational phase calculations for a mixture of toluene, methanol and water, similar to that illustrated in FIG. 4A, the number of required phase calculations has been reduced from 54 to about 12, both by the particular points in phase space for phase calculations being better selected, and by improved interpolation between these particular points in phase space. More generally, the saving in computational effort may for example be in the region from about 75% saved to about 90% saved using embodiments of the invention.

Having populated the phase diagram at step 20, particular concentrations of the component substances and if desired other parameters of the phase diagram may be chosen and used to formulate in step 40 a particular mixture of the substances which is expected to have the properties indicated by the phase diagram and therefore the intended properties and behaviour in use. The mixture may then be made at step 50, and optionally used in various ways as appropriate to the mixture at step 60, for example as an end product or as a feedstock or intermediary in another manufacturing process.

Since thermodynamic and other parameters such as temperature and pressure may also be parameters of the phase diagram, in step 50 the mixture may be used under one or more controlled ranges of such parameters where the desired phase properties are achieved.

To this end, embodiments of the invention provide a method of manufacturing or making a mixture of substances such as a mixture of liquids, the method comprising populating a phase diagram for the substances using the methods or apparatus described herein, using the phase diagram to specify parameters of the mixture to be made, and making the mixture according to the specified parameters.

The described method and system use a combination of methods derived from Bayesian optimization and sophisticated interpolation techniques to reduce the computational expense of calculating phase diagrams, whilst simultaneously increasing the information resolution obtained. The described method makes calculating phase diagrams faster than existing implementations and also achieves a higher resolution than current technology allows.

A Bayesian optimization process called maximum entropy sampling, which is a procedure for efficiently exploring a set of variables, is used to produce a maximally informative subset with minimal sampling. This requires the use of a Bayesian algorithm such as a Gaussian process that is capable of predicting both a value and the uncertainty related to the prediction. This is used with sophisticated interpolation techniques for generating the simulated phase diagrams.

Maximum entropy sampling is typically applied in the field of machine learning to select subsets of variables (for instance, constructing a training set), which includes a maximal amount of information for a minimal amount of sampling. Maximum entropy sampling samples a selection of points that have the highest predicted uncertainty and thus once calculated will contribute the most information to the model. This can be understood as the efficient selection of examples for constructing a set from which to develop a model. The described method optimizes the simulations that are to be performed to minimize calculation and the reconstruction of the phase diagram from these simulations. It is noted that the simulations themselves, and their accuracy, is not covered within the scope of this description as known methods may be used.

Typically, phase diagrams are calculated using a regular grid, where each point represents a simulation, which is either sequentially or batch executed using a high-performance computing system. By moving to a paradigm where calculation points are selected based upon their predicted information content, rather than their index, the generation of redundant information is eliminated thus reducing the computational cost of calculating the phase diagram.

The resolution of the resulting phase diagram is increased by using the resulting model to predict values for intermediate points, resulting in the ability to calculate the phase diagram at arbitrary levels of resolution.

Phase diagrams are used in many applications that need to show conditions (pressure, temperature, volume, etc.) at which distinct phases, such as thermodynamically distinct phases, of substances occur and coexist at equilibrium.

Figure 2:
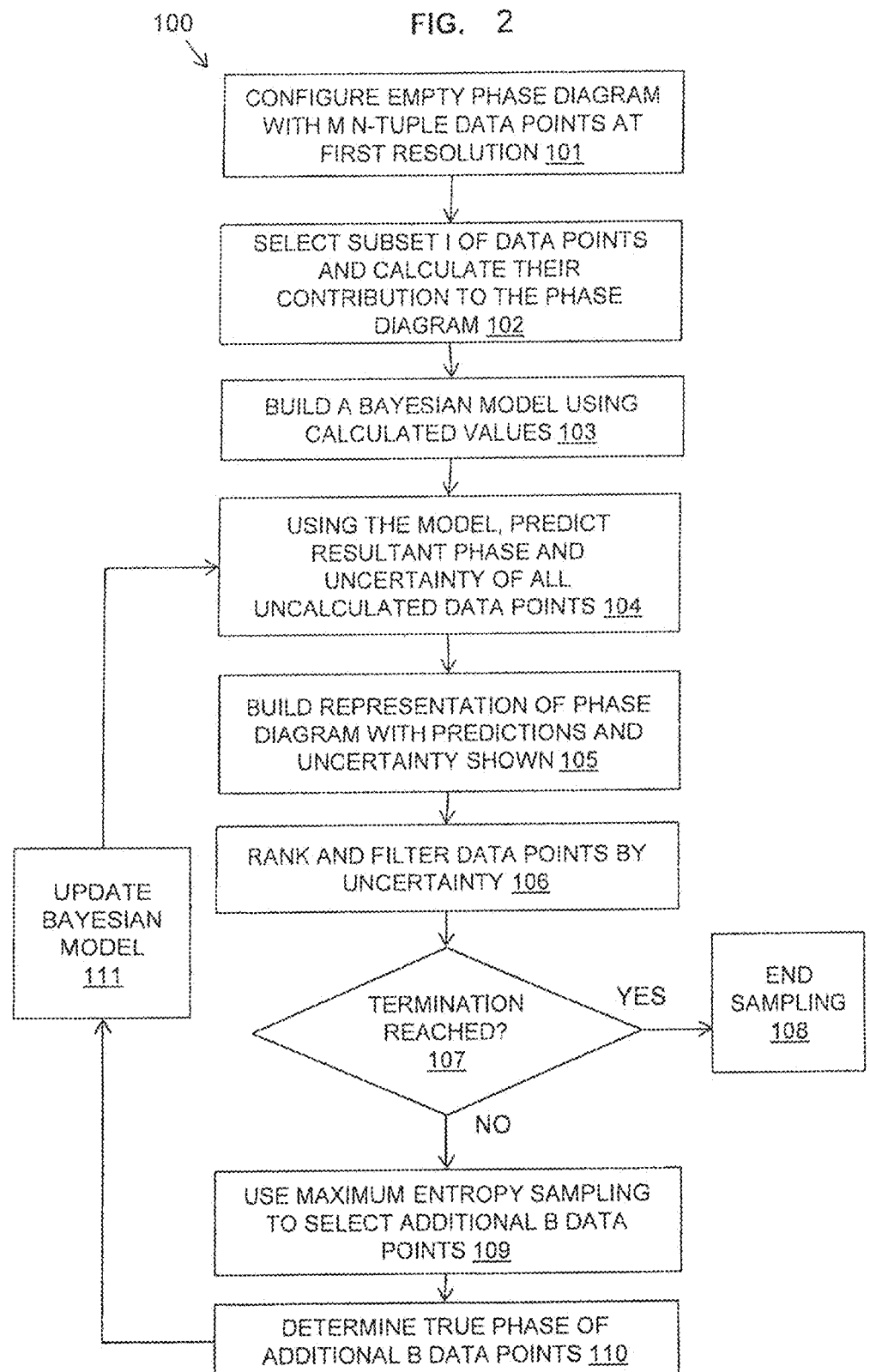
FIG. 2 is a flow diagram of an example embodiment of a method in accordance with the present invention.

Referring to FIG. 2, a flow diagram shows an example embodiment of the described method.

An n-way phase diagram may be defined 101 having data points with each data point being an n-tuple describing n substance inputs. The area encompassed by the phase diagram may be enumerated to a resolution desired by the user.

This method may be applied to a phase diagram containing any number of dimensions. For ease of understanding, the described embodiment assumes a ternary (3D) (i.e. 3-way)D) phase diagram and its associated triples. In the described example, the phase diagram may be a phase separation diagram for modeling the mixing of n liquid chemical components and their separation into distinct phases. For example, the liquid chemical components may be formulation liquid components, with the diagram comprising data points each representing an n-tuple describing the n chemical component inputs though their concentrations. The phases predicted are exampled by, but not limited to, branched worm-like, lamella, hexagonal, isotropic, cubic lattice, rods, worm-like and inverse micellar, and the reverse of these for high surfactant systems.

For a ternary phase diagram, for example, which describes the mixing of three components, this can be described using 3-Dimensional Barycentric coordinates with each triple describing the input for a simulation. This method may be applied to a phase diagram containing any number of dimensions; however, for ease of understanding, the method is described assuming a ternary (3D) phase diagram and its associated triples. In n dimensions, these triples would be replaced with an n-tuple.

From this set of coordinates, an initial subset of data points may be selected 102, and their contribution to the phase diagram (i.e. the resultant phase) calculated. The selection of the initial subset of data points may be very small with the only restriction being that there must be at least two data points. In practice, the subset may be in the order of 5% of the total data points.

The initial subset of data points may be selected randomly. Alternatively, the random sampling may be replaced with data that has already been acquired, thereby allowing the method to make maximal utility of any existing prior knowledge.

The calculation of this contribution of the subset of data points to the phase diagram is outside the scope of the described method. The calculation of the contribution may be by simulation methods or by experimental methods.

Typical methods of simulation for liquid formulation applications include but are not limited to molecular dynamics, Monte Carlo simulations, and Dissipative Particle Dynamics (DPD). In an example implementation based on dissipative particle dynamics, this is a stochastic simulation technique similar to coarse-grained molecular dynamics. In this technique, collections of individual atoms are replaced with single beads, and the energy and force is calculated using a simple physical model containing pairwise interactions and random forces. DPD is used as it gives access to longer timescales than traditional molecular dynamics approaches, allowing the simulation to address complex mesoscale behaviour, such as phase separation.

From the results of this calculation, a Bayesian model may be built 103 to map the coordinates to the resultant phase. The requirements of this model are that it has the ability to return both an uncertainty as well as a prediction for any given input. Thus suitable models might be, but are not limited to, Gaussian processes and Bayesian neural networks.

In Bayesian models, since the objective function is unknown, the Bayesian strategy is to treat it as a random function and place a "prior probability function" over it. A prior probability, also known as a "prior", of an uncertain quantity is the probability function that expresses beliefs about the quantity before evidence has been taken into account. The prior captures beliefs about the behaviour of the function. After gathering the function evaluations, which are treated as evidence, the prior is updated to form the posterior distribution over the objective function. The posterior distribution, in turn, is used to construct an acquisition function (often also referred to as infill sampling criteria) that determines what the next query point should be.

A Gaussian process is an actualization of the mathematical construct, the stochastic process that is a collection of random variables that has the property that the joint distribution of any subset of them is Gaussian. A Gaussian process is in the family of non-parametric methods, and is defined via a mean function, and a covariance function, sometimes called a kernel.

In one embodiment, a Gaussian process may be used for both the interpolation and the prediction, although a mixture of methods may be used. In a simple case, where a Gaussian process is used for both prediction and interpolation, a classification model is built by building a model that predicts the likelihood of each class, given the input features. The classification and certainty are built from this model's predictions over the range of potential classes compared to the data points already observed. Once this model is built, the interpolation is performed by predicting the outcomes of the as yet unobserved inputs (n-tuples) from the phase diagram. Since this model represents a continuous prediction, the resolution of the interpolation is not constrained to the resolution of the sampling and can be greater if desired.

A Bayesian neural network is an extension to the artificial neural network model. In an artificial neural network, signals (inputs) are propagated through a collection of neurons, whose response is based upon an activation function, which is typically non-linear. These activations are passed from neurons in one layer into the next layer through a combination procedure, typically a summation, where the contributions of each neuron are weighted through a weighting factor. The differentiation factor of a Bayesian neural network is that the weighting factors are described by distributions, typically Gaussians, rather than the point values, and represent the Bayesian prior over the weighting functions for the neural network.

The resultant model predicts 104 the phase for all triples for which no calculation has been performed, along with the uncertainty associated with that prediction. The uncertainty may be considered to be the error associated with the prediction and represents the width of the distribution of the predicted value. The results of these predictions may be used to build a representation 105 of the phase diagram at the resolution configured by the user when defining the phase diagram. Traditionally, representations of phase diagrams colour each point with a colour chosen to represent a particular phase. In this method, the representation is enhanced by choosing to set the alpha channel of the phase colour to a figure representative of the uncertainty of the prediction. This gives the user visual clues as to the trust that is appropriate to place on the prediction. The alpha channel is a logical choice for representing uncertainty as it maps evenly across colour palettes. However, any other transparency method may be used. In another embodiment, a colour channel, which is orthogonal to the others used in the method, may be used.

In a further alterative, the colour may be set by blending colours of potential other phases as represented by their uncertainty (i.e. a point which was 90% certain to be of phase 1 (red) and 10% of phase 2 (blue) would be a 90:10 red:blue blend). In another embodiment of the present invention, a colour channel could be replaced by grey scale. In another embodiment of the present invention, a colour channel could be replaced by shading. Representations of phase diagrams shade each point with a shade direction chosen to represent a particular phase. In this method, the representation is enhanced by adapting the shading to a figure representative of the uncertainty of the prediction.

The data points may be ranked 106 by their associated model uncertainty in order to use maximum entropy sampling with the largest value for uncertainty in model prediction chosen and the phase for the most uncertain triple selected to be calculated next. This approach may be parallelized by the selection of multiple triples, with the addition of a redundancy filter, if necessary. This avoids data points which contribute similar information to the model and thus, which adding to the prior would provide a large amount of redundant information. This redundancy filter may be implemented through ordering the triples by their uncertainty and then clustering together similar triples. The centroid of each cluster is then treated as representative of the whole cluster. The clustering may be achieved by thresholding a Euclidean distance and may be performed in conjunction with the selection of the next points to sample. Thus, the workflow may be: i) predict value and uncertainty of un-sampled points, ii) perform redundancy filtering, and iii) choose next points from the filtered set.

This method may be performed serially with the model being updated at each iteration to avoid adding points that contribute the same information into the model, thus reducing the efficiency. Redundancy filtering or clustering is a method for allowing the parallelization of the workload. It works by clustering together points that are predicted to add similar information to the model, so that each point that is added during an iteration contributes significantly different information to the model. The method may determine 107 if a termination criterion has been reached before iterating another maximum entropy sampling. If the termination criterion has been reached, then the sampling is terminated 108.

In one embodiment, the average uncertainty for the phase diagram may be determined through averaging the calculated uncertainty for all points in the set. If this value is below a threshold (i.e. the overall confidence is high), the sampling is terminated before any more data is acquired. The value of the threshold may be user determined, and is a measure of the desired accuracy of the model. One method for determining a relevant value would be to choose a value related to the accuracy and precision available from experimental measurement.

In another embodiment, the sampling may be terminated if the change in uncertainty (the gradient) converges. In a further embodiment, a set number of iterations may be carried out although it is hard to put a number on this as it is dependent on the complexity of the problem (e.g. number of phases) and the number of dimensions (i.e. a 10-component mixture would most likely require a significantly greater number of samples than a 3-component mixture.) A fixed-iteration implementation may be provided that may limit the number of iterations to a fixed compute time.

If the termination criterion has not been reached, maximum entropy sampling is used 109 to select an additional B data points. Maximum entropy sampling samples a selection of points that have the highest predicted uncertainty and, once calculated, will contribute the most information to the model. The true phase of the additional B data points may be determined and the Bayesian model may be updated 111.

The method may iterate to repeat the prediction 104 of the resultant phase and associated uncertainty of all the uncalculated data points, building 105 the representation of the phase diagram, ranking 106 the data points by uncertainty, and determining if a termination criterion has been reached 107.

The sample size B may be constant or variable. If it is variable, it may be dependent on a threshold of desired amount of information entropy (i.e. the uncertainty). The efficiency gain through the use of this approach for the calculation of phase diagrams may be calculated for a constant sample size B using the following formula:

$$E = \frac{I + (N_{stages} * B)}{N_{total}}$$

Where I is the size of the initially selected randomly sampled set, B is the number of points added at each sampling stage, Nstages is the number of stages (rounds) of sampling, and Ntotal is the number of points which are created by grid sampling the phase diagram at the desired resolution.

Figure 3:
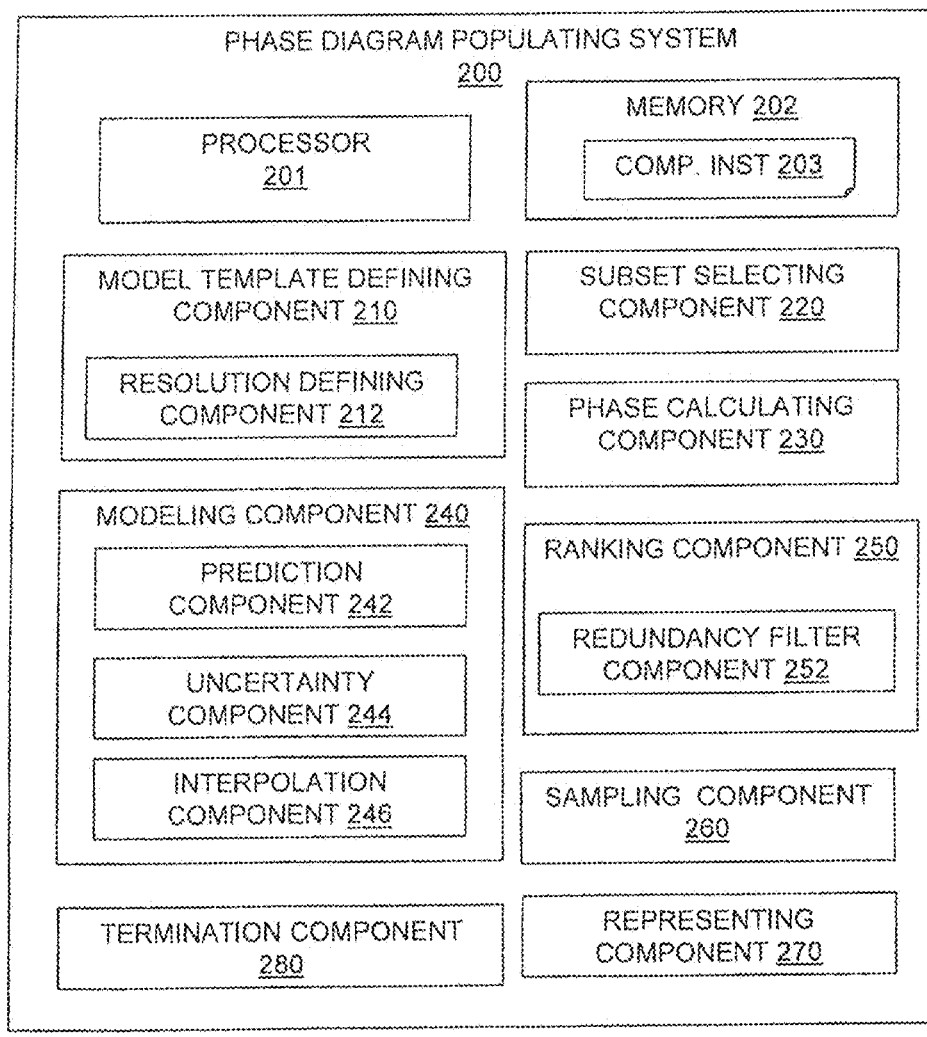
FIG. 3 is block diagram of an example embodiment of a system in accordance with the present invention.

Referring to FIG. 3, a block diagram shows an example embodiment of the described system in the form of a phase diagram populating system 200.

The phase diagram populating system 200 may include at least one processor 201, a hardware module, or a circuit for executing the functions of the described components which may be software units executing on the at least one processor. Multiple processors running parallel processing threads may be provided enabling parallel processing of some or all of the functions of the components. Memory 202 may be configured to provide computer instructions 203 to the at least one processor 201 to carry out the functionality of the components.

The phase diagram populating system 200 may include a template defining component 210 for defining an n-way phase diagram with M data points each being an n-tuple describing then substance inputs. The template defining component 210 may include a resolution defining component 212 for inputting a defined user-configured resolution for the phase diagram.

The phase diagram populating system 200 may include a subset selecting component 220 for selecting an initial subset of data points. The subset of data points may be randomly selected or may be data points having data that has already been acquire. The phase diagram populating system 200 may include a phase calculating component 230 for calculating the contribution of the subset of data points to the phase diagram. This may be carried out by simulation of the data points or by experiment to gather phase data. The phase calculating component 230 may subsequently calculate the contribution of sampled data points sampled by a sampling component 260 described below.

The phase diagram populating system 200 may include a modelling component 240 for generating a Bayesian model based initially on the subset of calculated data points and later on the sample data points for which their phase is calculated.

The modeling component 240 may include a prediction component 242 for predicting the resultant phase of uncalculated data points in the defined phase diagram, an uncertainty component 244 for modeling an associated uncertainty of the uncalculated data points, and an interpolation component 246 for interpolating the data points for the defined resolution. The modeling component 240 may use, for example, a Gaussian process or a Bayesian neural network including prediction and interpolation of data points in the model.

The modeling component 240 may re-model the model during method iterations of subsequent sample selections.

The phase diagram populating system 200 may include a ranking component 250 for ranking the data points by their associated uncertainty in order to use maximum entropy sampling of the largest values for uncertainty. The ranking component 250 may include a redundancy filter component 252 for applying a redundancy filter through ranking the data point by their uncertainty and then clustering together similar data points parallelizing the selection of multiple data points.

The phase diagram populating system 200 may include a sampling component 260 for selecting a subset m of the M data points using maximum entropy sampling and calculating a resultant phase for each of the m selected data points, and incorporating the calculated phases into the Bayesian model and for repeating the selecting until a defined termination criterion is met. The phase diagram populating system 200 may include a representation component 270 for providing a representation of the phase diagram including a representation of the uncertainty values of the data points and updating the representation of the phase diagram for each maximum entropy sampling. The representation component 270 may represent the phases of the phase diagram using colour shades, wherein the alpha channel of a colour shade is set relative to the uncertainty of the phase. In an alternative embodiment, the representation component 270 may represent the phases of the phase diagram using grey scale shades, or shading, wherein the alpha channel of a grey scale, or density of shading is set relative to the uncertainty of the phase.

The phase diagram populating system 200 may include a termination component 280 for terminating the method when a termination criterion is reached. The termination criterion may be: a configured time period for the sampling, a configured number of iterations of sampling, a target uncertainty is reached, a converging uncertainty is reached.

Figure 4B:
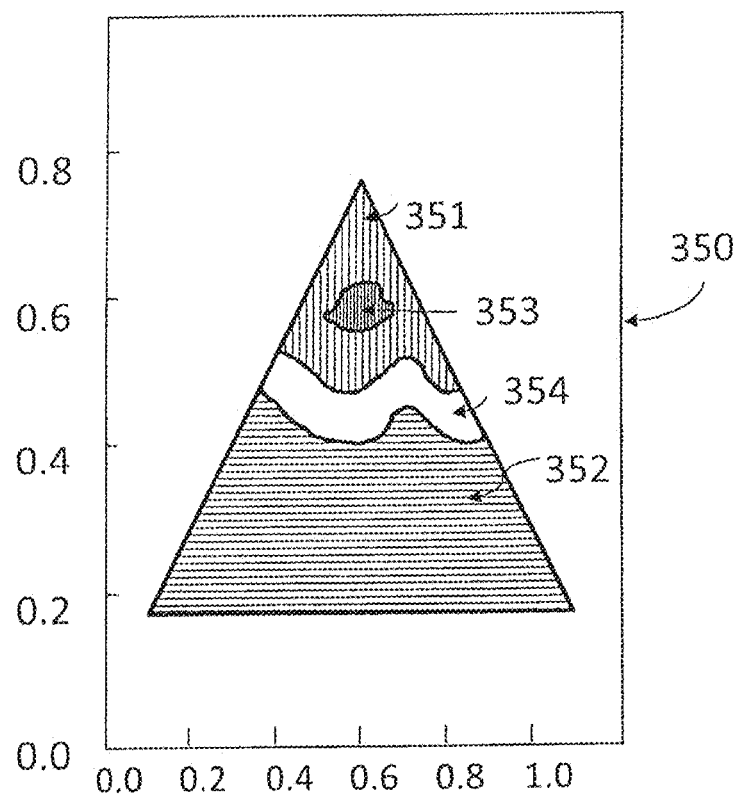

Referring to FIGS. 4A and 4B, example phase diagrams 300, 350 are shown for ternary phase diagram for mixing and separation of the three substances of water, methanol and toluene.

The phase diagram 300 of FIG. 4A is an example of the use of the prior art method for calculating a ternary phase diagram, consisting of a regular grid of 54 points. The diagram 300 shows the top of the triangle as mixed substances 301 with a phase boundary with separated substances 302. A line 303 shows the edges of the phase boundary of separated substances and a line 304 shows the edges of the phase boundary of mixed substances.

The phase diagram 350 of FIG. 4B is an example phase diagram output using the described method. This uses far fewer points for calculating the phase diagram (in this example, 14 points (not shown)) and outputs a phase diagram with an effective 500,500 points. The resolution increase is performed through the use of the Bayesian model to predict the phase (in this example, mixed or separated) at points on a significantly denser grid. In this example, the mixed phase 351 is represented in cross-hatched shading and the separated phase is represented in diagonal striped shading 352. The alpha channel (transparency) in this image represents the uncertainty in the prediction, with greater density cross-hatched shading points, for example points in the middle 353 of the mixed phase, being more certain than lighter ones, for example points in the boundary 354 between the phases. In practice, the shading and the alpha channel transparency (for example, density of shading) would be graduated between phases resulting in different tones whereas this is shown as distinct lines in the figure for simplicity of illustration.

In one embodiment, the n-way phase diagram is a phase separation diagram for substances in the form of liquid chemical compounds for modeling of the mixing of n liquid chemical components. The method accelerates the modeling of mixing multiple chemical components for liquid formulation by generating the simulated phase diagrams. In the field of liquid formulation, the construction of a phase diagram is important to indicate where mixtures will begin to separate into their constituent components.

In another example embodiment, a temperature/pressure phase diagram of gas mixtures may be modeled for refrigerant.

The described method and system use additional optimization features built on top of the existing art for the accelerating and enriching of the calculation of phase diagrams, and the use of a sophisticated interpolative model for predicting the behaviour of intermediate points that increases the resolution capacity over current methods.

The described method uses a means for accelerating the calculation of a phase diagram through the combination of a Bayesian algorithm to select the area in which to perform a simulation so that the maximum amount of information is gained with a data driven model built from the resulting information, which is used to reconstruct the rest of the phase diagram to a high level of resolution. The described method accelerates the calculation of a single phase diagram based upon real-time information and by using the principles of maximum entropy sampling reduces the computational cost associated with the population of phase diagrams.

Figure 5:
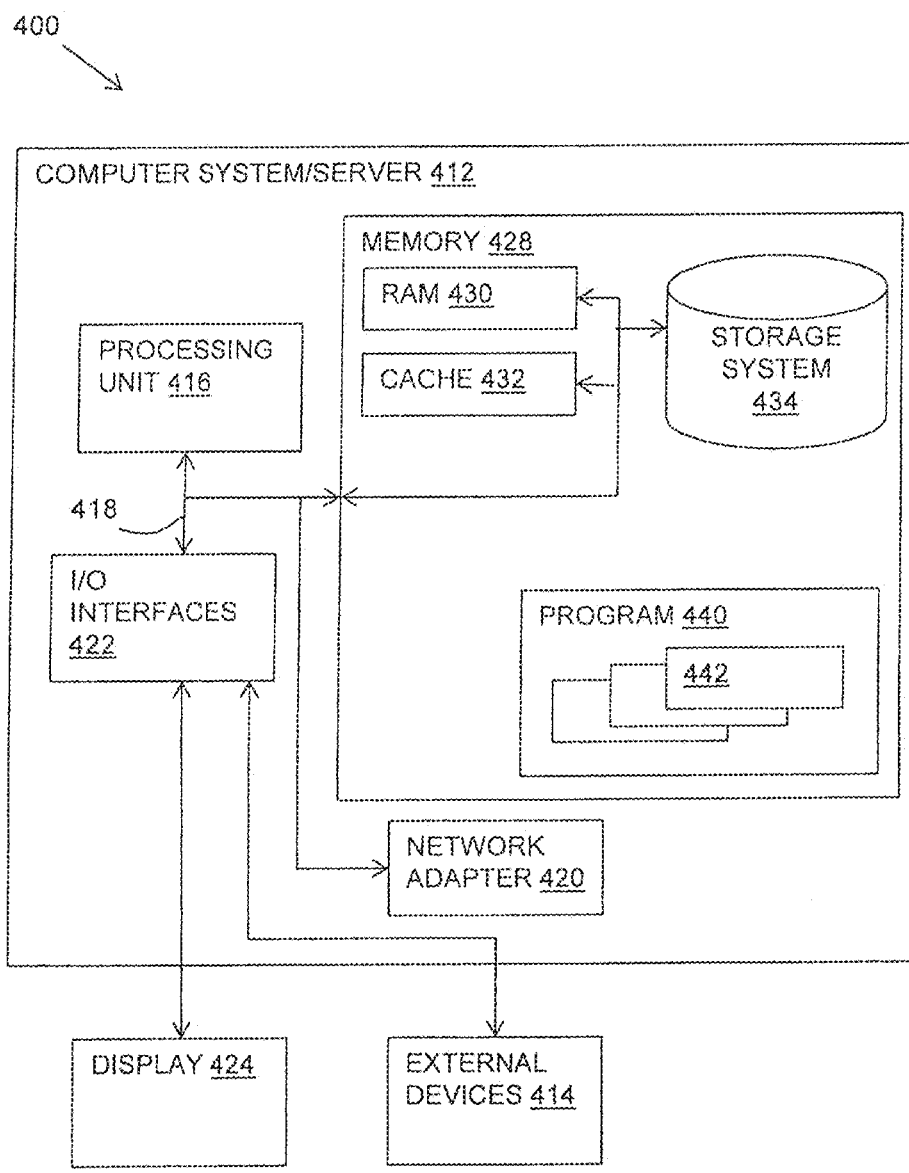
FIG. 5 is a block diagram of an embodiment of a computer system or cloud server in which the present invention may be implemented.

Referring now to FIG. 5, a schematic of an example of a system 400 in the form of a computer system or server is shown.

A computer system or server 412 may be operational with numerous other general purpose or special purpose computing system environments or configurations. Examples of well-known computing systems, environments, and/or configurations that may be suitable for use with computer system/server 412 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 412 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 412 may be practiced in distributed cloud computing environments where tasks are performed by remote processing devices that are linked through a communications network. In a distributed cloud computing environment, program modules may be located in both local and remote computer system storage media including memory storage devices.

In FIG. 5, a computer system/server 412 is shown in the form of a general-purpose computing device. The components of the computer system/server 412 may include, but are not limited to, one or more processors or processing units 416, a system memory 428, and a bus 418 that couples various system components including system memory 428 to processor 416. Bus 418 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 412 typically includes a variety of computer system readable media. Such media may be any available media that is accessible by computer system/server 412, and it includes both volatile and non-volatile media, removable and non-removable media.

System memory 428 can include computer system readable media in the form of volatile memory, such as random access memory (RAM) 430 and/or cache memory 432. Computer system/server 412 may further include other removable/non-removable, volatile/non-volatile computer system storage media. By way of example only, storage system 434 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 418 by one or more data media interfaces. As will be further depicted and described below, memory 428 may include at least one program product having a set (e.g., at least one) of program modules that are configured to carry out the functions of embodiments of the invention.

Program/utility 440, having a set (at least one) of program modules 442, may be stored in memory 428 by way of example, and not limitation, as well as an operating system, one or more application programs, other program modules, and program data. Each of the operating system, one or more application programs, other program modules, and program data or some combination thereof, may include an implementation of a networking environment. Program modules 442 generally carry out the functions and/or methodologies of embodiments of the invention as described herein.

Computer system/server 412 may also communicate with one or more external devices 414 such as a keyboard, a pointing device, a display 424, etc.; one or more devices that enable a user to interact with computer system/server 412; and/or any devices (e.g., network card, modem, etc.) that enable computer system/server 412 to communicate with one or more other computing devices. Such communication can occur via Input/Output (I/O) interfaces 422. Still yet, computer system/server 412 can communicate with one or more networks such as a local area network (LAN), a general wide area network (WAN), and/or a public network (e.g., the Internet) via network adapter 420. As depicted, network adapter 420 communicates with the other components of computer system/server 412 via bus 418. It should be understood that although not shown, other hardware and/or software components could be used in conjunction with computer system/server 412. Examples, include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Cloud Computing

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 6:
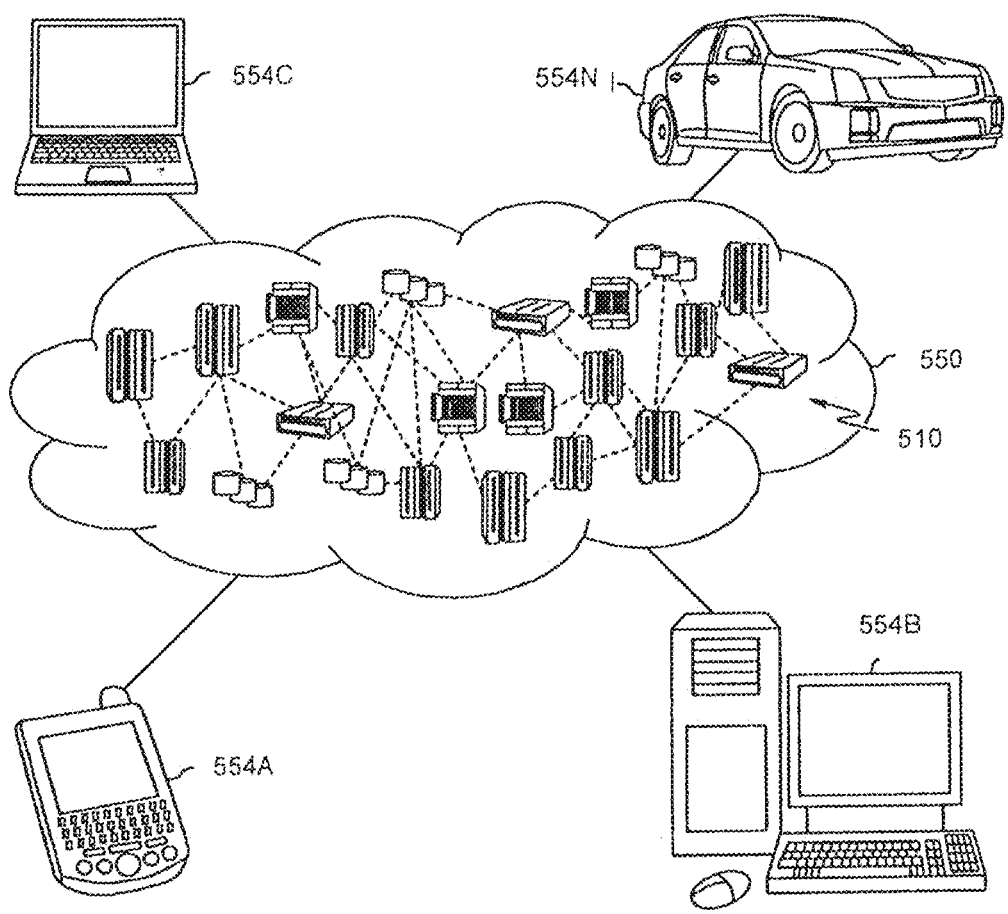
FIG. 6 is a schematic diagram of a cloud computing environment in which the present invention may be implemented.

A cloud computing environment is service oriented with a focus on statelessness, low coupling, modularity, and semantic interoperability. At the heart of cloud computing is an infrastructure that includes a network of interconnected nodes. Referring now to FIG. 6, illustrative cloud computing environment 550 is depicted. As shown, cloud computing environment 550 includes one or more cloud computing nodes 510 with which local computing devices used by cloud consumers, such as, for example, personal digital assistant (PDA) or cellular telephone 554A, desktop computer 554B, laptop computer 554C, and/or automobile computer system 554N may communicate. Nodes 510 may communicate with one another. They may be grouped (not shown) physically or virtually, in one or more networks, such as Private, Community, Public, or Hybrid clouds as described hereinabove, or a combination thereof. This allows cloud computing environment 550 to offer infrastructure, platforms and/or software as services for which a cloud consumer does not need to maintain resources on a local computing device. It is understood that the types of computing devices 554A-N shown in FIG. 5 are intended to be illustrative only and that computing nodes 510 and cloud computing environment 550 can communicate with any type of computerized device over any type of network and/or network addressable connection (e.g., using a web browser).

Figure 7:
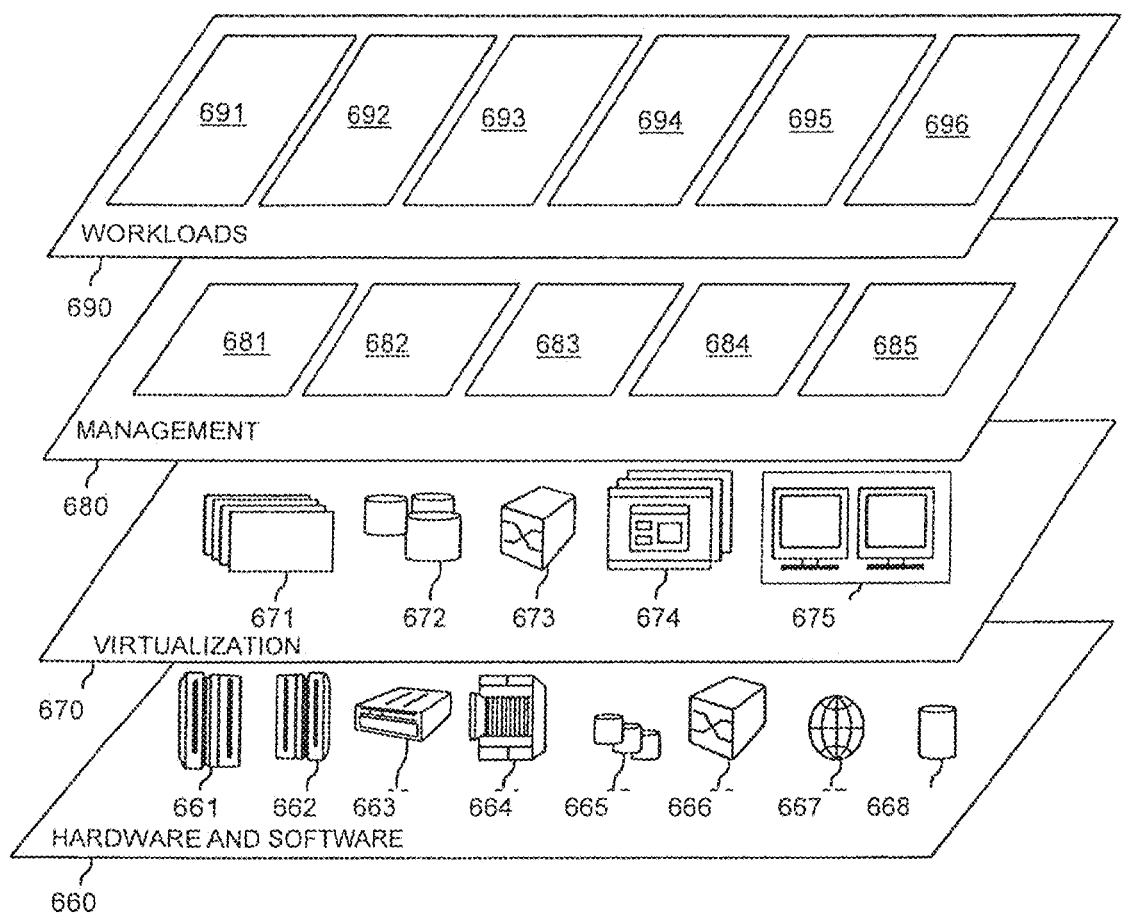
FIG. 7 is a diagram of abstraction model layers of a cloud computing environment in which the present invention may be implemented.

Referring now to FIG. 7, a set of functional abstraction layers provided by cloud computing environment 550 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 660 includes hardware and software components. Examples of hardware components include: mainframes 661; RISC (Reduced Instruction Set Computer) architecture based servers 662; servers 663; blade servers 664; storage devices 665; and networks and networking components 666. In some embodiments, software components include network application server software 667 and database software 668. Virtualization layer 670 provides an abstraction layer from which the following examples of virtual entities may be provided: virtual servers 671; virtual storage 672; virtual networks 673, including virtual private networks; virtual applications and operating systems 674; and virtual clients 675. In one example, management layer 680 may provide the functions described below. Resource provisioning 681 provides dynamic procurement of computing resources and other resources that are utilized to perform tasks within the cloud computing environment. Metering and Pricing 682 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 683 provides access to the cloud computing environment for consumers and system administrators. Service level management 684 provides cloud computing resource allocation and management such that required service levels are met. Service Level Agreement (SLA) planning and fulfilment 685 provide pre-arrangement for, and procurement of, cloud computing resources for which a future requirement is anticipated in accordance with an SLA.

Workloads layer 690 provides examples of functionality for which the cloud computing environment may be utilized. Examples of workloads and functions which may be provided from this layer include: mapping and navigation 691; software development and lifecycle management 692; virtual classroom education delivery 693; data analytics processing 694; transaction processing 695; and data modelling processing 696.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Improvements and modifications can be made to the foregoing without departing from the scope of the present invention.

The invention claimed is:

1. A computer program product for efficiently populating a phase diagram for multiple substances, the computer program product stored on a non-transitory computer readable medium and loadable into the internal memory of a digital computer, comprising software code portions, when said program is run on a computer, for presentation of a graphical user interface, the graphical user interface comprising: axes representing parameters of at least a portion of a phase diagram fora mixture of substances; and pixel rendering located relative to the axes, the pixel rendering comprising pixel coloring representing determined phases of the mixture of substances within the phase diagram, wherein the pixel rendering also represents calculated uncertainties of the determined phases, and wherein the program, to determine the determined phases and uncertainties, is further configured to: define an n-way phase diagram with data points each being an n-tuple describing the n substance inputs, wherein the n-way phase diagram is defined at a user-configured resolution; select an initial subset of data points and calculate their contribution to the phase diagram; generate a Bayesian model based on the initial subset of calculated data points and predict the resultant phase and an associated uncertainty of all the uncalculated data points in the defined phase diagram; select a sample subset of the data points using maximum entropy sampling and calculate a resultant phase for each of the selected data points, and incorporate the calculated phases into the Bayesian model; re-model the Bayesian model to predict the resultant phase and an associated uncertainty of all the remaining uncalculated data points in the defined phase diagram; and repeat the selecting a sample subset of the data points using maximum entropy sampling and re-modeling until a defined termination criterion is met.

2. The computer program product of claim 1 wherein the pixel rendering represents calculated uncertainties of the determined phases using one or more transparency properties of the pixel rendering.

3. The computer program product of claim 1 arranged to update the representation of the phase diagram for each maximum entropy sampling.

4. The computer program product of claim 1 wherein the pixel coloring represents determined phases of the mixture of substances using color shades, wherein the alpha channel of a color shade is set relative to the uncertainty of a determined phase.

5. The computer program product of claim 1 wherein the program, to determine the determined phases and uncertainties, is further configured: rank the data points by their associated uncertainty in order to use maximum entropy sampling of the largest values for uncertainty including application of a redundancy filter through ranking the data points by their uncertainty and clustering together similar data points parallelizing the selection of data points.

6. The computer program product of claim 1 wherein the program, to predict the resultant phase and an associated uncertainty of all the uncalculated data points, is further configured to predict in parallel by processing multiple data points.

7. The computer program product of claim 1, wherein the selection of an initial subset of data points selects a random subset of data points or selects a known subset of data points for which data has been acquired.

8. The computer program product of claim 1, wherein the calculation of the data points' contribution to the phase diagram is carried out by simulation or experimentation.

9. The computer program product of claim 1, wherein the generation of the Bayesian model uses a Gaussian process including prediction and interpolation of data points in the model.

10. The computer program product of claim 1, wherein the generation of the Bayesian model uses a Bayesian neural network including prediction and interpolation of data points in the model.

11. The computer program product of claim 1, wherein the termination criterion is one of the group of: a configured time period for the sampling; a configured number of iterations of sampling; a target uncertainty is reached; and a converging uncertainty is reached.

12. A graphical user interface comprising:
axes representing parameters of at least a portion of a phase diagram for a mixture of substances; and
pixel rendering located relative to the axes, the pixel rendering comprising pixel coloring representing determined phases of the mixture of substances within the phase diagram,
wherein the pixel rendering also represents calculated uncertainties of the determined phases, and
wherein the determined phases and uncertainties are determined via:
definition of an n-way phase diagram with data points each being an n-tuple describing the n substance inputs, wherein the n-way phase diagram is defined at a user-configured resolution;
selection of an initial subset of data points and calculation of their contribution to the phase diagram;
generation of a Bayesian model based on the initial subset of calculated data points and prediction of the resultant phase and an associated uncertainty of all the uncalculated data points in the defined phase diagram;
selection of a sample subset of the data points using maximum entropy sampling and calculation of a resultant phase for each of the selected data points, and incorporating the calculated phases into the Bayesian model;
a re-model of the Bayesian model to predict the resultant phase and an associated uncertainty of all the remaining uncalculated data points in the defined phase diagram; and
repetition of the selection of a sample subset of the data points using maximum entropy sampling and re-modeling until a defined termination criterion is met.

13. The graphical user interface of claim 12 wherein the pixel rendering represents calculated uncertainties of the determined phases using one or more transparency properties of the pixel rendering.

14. The graphical user interface of claim 12 arranged to update the representation of the phase diagram for each maximum entropy sampling.

15. The graphical user interface of claim 12 wherein the pixel coloring represents determined phases of the mixture of substances using color shades, wherein the alpha channel of a color shade is set relative to the uncertainty of a determined phase.

16. The graphical user interface of claim 12 wherein the determined phases and uncertainties are further determined via:
a ranking of the data points by their associated uncertainty in order to use maximum entropy sampling of the largest values for uncertainty including an application of a redundancy filter through ranking the data points by their uncertainty and clustering together similar data points parallelizing the selection of data points.

17. The graphical user interface of claim 12 wherein the prediction of the resultant phase and an associated uncertainty of all the uncalculated data points is performed in parallel by processing multiple data points.

18. The graphical user interface of claim 12, wherein the selection of an initial subset of data points comprises a selection of a random subset of data points or a selection of a known subset of data points for which data has been acquired.

19. The graphical user interface of claim 12, wherein the calculation of the data points' contribution to the phase diagram is carried out by simulation or experimentation.

20. The graphical user interface of claim 12, wherein the generation of the Bayesian model uses a Gaussian process including prediction and interpolation of data points in the model.

21. The graphical user interface of claim 12, wherein the generation of the Bayesian model uses a Bayesian neural network including prediction and interpolation of data points in the model.

22. The graphical user interface of claim 12, wherein the termination criterion is one of the group of: a configured time period for the sampling; a configured number of iterations of sampling; a target uncertainty is reached; and a converging uncertainty is reached.

23. The graphical user interface of claim 12, wherein the n-way phase diagram is a phase separation diagram for substances in the form of liquid chemical compounds for modeling of the mixing of n liquid chemical components.

24. The graphical user interface of claim 12, wherein the phase diagram is used to specify parameters of the mixture which is made according to the specified parameters.

25. A system comprising:
a processor and a memory coupled therewith, the memory comprising computer executable instructions that when executed by the processor, cause the processor to:
generate a graphical user interface presented on a display coupled with the processor, the graphical user interface comprising:
axes representing parameters of at least a portion of a phase diagram for a mixture of substances; and
pixel rendering located relative to the axes, the pixel rendering comprising pixel coloring representing determined phases of the mixture of substances within the phase diagram,
wherein the pixel rendering also represents calculated uncertainties of the determined phases, and
wherein the computer executable instructions, to determine the determined phases and uncertainties, are further executable by the processor to cause the processor to:
define an n-way phase diagram with data points each being an n-tuple describing the n substance inputs, wherein the n-way phase diagram is defined at a user-configured resolution;
select an initial subset of data points and calculate their contribution to the phase diagram;
generate a Bayesian model based on the initial subset of calculated data points and predict the resultant phase and an associated uncertainty of all the uncalculated data points in the defined phase diagram;
select a sample subset of the data points using maximum entropy sampling and calculate a resultant phase for each of the selected data points, and incorporate the calculated phases into the Bayesian model;
re-model the Bayesian model to predict the resultant phase and an associated uncertainty of all the remaining uncalculated data points in the defined phase diagram; and
repeat the selecting a sample subset of the data points using maximum entropy sampling and re-modeling until a defined termination criterion is met.

26. A computer implemented method comprising:
generating, by a processor, a graphical user interface for presentation on a display coupled with the processor, the graphical user interface comprising:
axes representing parameters of at least a portion of a phase diagram for a mixture of substances; and
pixel rendering located relative to the axes, the pixel rendering comprising pixel coloring representing determined phases of the mixture of substances within the phase diagram,
wherein the pixel rendering also represents calculated uncertainties of the determined phases, and
the method further comprising determining the determined phases and uncertainties by:
defining, by the processor, an n-way phase diagram with data points each being an n-tuple describing the n substance inputs, wherein the n-way phase diagram is defined at a user-configured resolution;
selecting, by the processor, an initial subset of data points and calculate their contribution to the phase diagram;
generating, by the processor, a Bayesian model based on the initial subset of calculated data points and predicting the resultant phase and an associated uncertainty of all the uncalculated data points in the defined phase diagram;
selecting, by the processor, a sample subset of the data points using maximum entropy sampling and calculating a resultant phase for each of the selected data points, and incorporating the calculated phases into the Bayesian model;
re-modeling, by the processor, the Bayesian model to predict the resultant phase and an associated uncertainty of all the remaining uncalculated data points in the defined phase diagram; and
repeating, by the processor, the selecting a sample subset of the data points using maximum entropy sampling and re-modeling until a defined termination criterion is met.

27. A non-transitory computer readable medium comprising computer executable instructions that when executed by a processor of the computer, cause the processor to: generate a graphical user interface presented on a display coupled with the processor, the graphical user interface comprising: axes representing parameters of at least a portion of a phase diagram fora mixture of substances; and pixel rendering located relative to the axes, the pixel rendering comprising pixel coloring representing determined phases of the mixture of substances within the phase diagram, wherein the pixel rendering also represents calculated uncertainties of the determined phases, and wherein the computer executable instructions, to determine the determined phases and uncertainties, are further executable by the processor to cause the processor to: define an n-way phase diagram with data points each being an n-tuple describing the n substance inputs, wherein the n-way phase diagram is defined at a user-configured resolution; select an initial subset of data points and calculate their contribution to the phase diagram; generate a Bayesian model based on the initial subset of calculated data points and predict the resultant phase and an associated uncertainty of all the uncalculated data points in the defined phase diagram; select a sample subset of the data points using maximum entropy sampling and calculate a resultant phase for each of the selected data points, and incorporate the calculated phases into the Bayesian model; re-model the Bayesian model to predict the resultant phase and an associated uncertainty of all the remaining uncalculated data points in the defined phase diagram; and repeat the selecting a sample subset of the data points using maximum entropy sampling and re-modeling until a defined termination criterion is met.

* * * * *

UNITED STATES PATENT AND TRADEMARK OFFICE
CERTIFICATE OF CORRECTION

PATENT NO. : 11,923,050 B2
APPLICATION NO. : 16/630197
DATED : March 5, 2024
INVENTOR(S) : Edward Pyzer-Knapp and Richard Anderson It is certified that error appears in the above-identified patent and that said Letters Patent is hereby corrected as shown below:

In the Claims

Claim 1, Column 17, Line 28:
Please change "fora" to "for a"

Claim 27, Column 21, Line 7:
Please change "fora" to "for a"

Signed and Sealed this
Ninth Day of April, 2024

Katherine Kelly Vidal
Director of the United States Patent and Trademark Office